United States Patent [19]
Forse et al.

[11] Patent Number: 5,821,217
[45] Date of Patent: *Oct. 13, 1998

[54] ENTERAL FORMULATION: LOW IN FAT AND CONTAINING PROTEIN HYDROLYSATES

[75] Inventors: R. Amour Forse, Brookline; Stacey J. Bell; Peter Burke, both of Belmont, all of Mass.

[73] Assignee: Beth Israel Deaconess Medical Center, Inc., Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 549,062

[22] Filed: Oct. 27, 1995

[51] Int. Cl.$^6$ .......................... A61K 38/00; A61K 31/70; A61K 31/715; A61K 31/22; A61K 31/23; A61K 31/20

[52] U.S. Cl. ................... 514/2; 514/23; 514/54; 514/60; 514/549; 514/552; 514/558; 514/560

[58] Field of Search ................... 514/2, 23, 54, 514/60, 549, 552, 558, 560

[56] References Cited

U.S. PATENT DOCUMENTS

| | | | |
|---|---|---|---|
| 3,698,912 | 10/1972 | Winitz | 514/2 |
| 4,438,144 | 3/1984 | Blackburn | 424/319 |
| 4,528,197 | 7/1985 | Blakburn | 514/552 |
| 4,959,350 | 9/1990 | Frokjaer et al. | 514/2 |
| 5,106,836 | 4/1992 | Clemens et al. | 514/21 |
| 5,189,016 | 2/1993 | Madsen et al. | 514/2 |
| 5,229,136 | 7/1993 | Mark et al. | 424/535 |
| 5,298,493 | 3/1994 | Mendy | 514/21 |
| 5,403,972 | 4/1995 | Valentine, Sr. | 84/730 |
| 5,405,835 | 4/1995 | Mendy | 514/21 |
| 5,438,042 | 8/1995 | Schmidl et al. | 514/21 |
| 5,545,411 | 8/1996 | Chancellor | 424/439 |

FOREIGN PATENT DOCUMENTS

| | | |
|---|---|---|
| 0 189 160 | 7/1986 | European Pat. Off. . |
| 0 189 161 | 7/1986 | European Pat. Off. . |
| 0 502 313 | 9/1992 | European Pat. Off. . |

OTHER PUBLICATIONS

Donald, P., et al., "Repletion of Nutritional Parameters in Surgical Patients Receiving Peptide Versus Amino Acid Elemental Fedings," *Nutrition Research*, vol. 14, 3–12 (1994);.

Dutton, E., et al., "Medium–Chain Triglycerides in Neonatal Nutrition," *American Journal of Perinatology*, vol. 4, No. 1, 5–7 (1987);.

Hamilton, C., et al., "Protocol Decreases Enteral Feeding Complications," *17th Clinical Congress Abstracts*, vol. 17, No. 1, supplement, 31S (Jan.–Feb. 1993);.

Heimburger, D.C. et al., "Tolerance and Efficacy of Small–Peptide Enteral Feeding Formula VS. Isocaloric, Isonitrogenous Whole–Protein Formula," *18th Clinical Congress Abstracts*, vol. 18, No. 1, supplement, 21S (Jan.–Feb. 1994);.

McBurney, M.I. et al., "Effect of Soy Polysaccharide (SP) Supplementation of Total Enteral Nutrition (TEN) Formulas on Large Bowel Short Chain Fatty Acid (SCFA) Production in Humans," *16th Clinical Congress Abstracts*, vol. 16, No. 1, supplement, 18S (Jan.–Feb. 1992);.

Mowatt–Larssen, C.A., "Enteral Nutrition Efficacy and Tolerance Comparison of Peptide with Standard Formulas," *15th Clinical Congress Abstracts*, vol. 15, No. 1, supplement, 32S (Jan.–Feb. 1991);.

Simko, V., et al., "Absorption of Diffrent Elemental Diets in a Short–Bowel Syndrome Lasting 15 Years," *Digestive Diseases*, vol. 21, No. 5, 419–425 (1976).

*Primary Examiner*—Raymond Henley, III
*Attorney, Agent, or Firm*—Hamilton, Brook, Smith & Reynolds, P.C.

[57] ABSTRACT

An improved enteral formulation that is low in fat and contains protein hydrolysates has been developed. The osmolality of the formulation is controlled to be below 500 mOs/kg $H_2O$, preferably about 300 mOs/kg $H_2O$. In a preferred embodiment, the formulation contains corn starch to control blood glucose levels. This formulation is particularly useful for treatment of critically ill patients and in minimizing a risk of pulmonary aspiration and/or gastrointestinal dysfunction in such patients.

12 Claims, No Drawings

ENTERAL FORMULATION: LOW IN FAT AND CONTAINING PROTEIN HYDROLYSATES

BACKGROUND OF THE INVENTION

Under normal nutritional and physiological conditions, fuel requirements of the body are met primarily by glucose and fatty acid metabolism. However, during abnormal metabolic stress, states induced by trauma such as operations or acute illnesses which lead to conditions such as sepsis, one of the effects is a decrease of fat and glucose utilization. More particularly, stress of injury in an individual, e.g., trauma or sepsis, is often accompanied by a total or partial dysfunction of the gastrointestinal tract. These critically ill individuals are often hospitalized and must receive most or all of their daily nutritional requirements passively in order to sustain protein synthesis and avoid malnutrition. Nutritional support therapy, particularly enteral tube feeding, may have advantageous effects in treating these patients.

It has been observed that patients who are critically ill, such as trauma or sepsis patients, in the intensive care unit and who are candidates for enteral nutrition by feeding tube, often do not tolerate existing, commercially-available formulas well. Poor tolerance is manifested as gastrointestinal-related symptoms of abdominal pain, bloating and diarrhea. These conditions are not life threatening but preclude the patient from receiving the full nutritional prescription; in fact, the tube feeding diet is usually stopped until the symptoms improve. Patients who receive the tube feeding formula into their stomach in contrast to the small bowel may aspirate their gastric contents into the lungs. This can be a very serious, life-threatening consequence of enteral nutrition and is relatively common in the critically ill patients because of the presence of multiple infections.

Commercially available tube feeding formulas are characterized by high fat content, such as those described in U.S. Pat. No. 5,438,042. These formulations, however, can be a problem since the high fat formulas are emptied slower than low fat formulas and may contribute to pulmonary aspiration and to abdominal discomfort and diarrhea.

Although some low fat formulations have been tested, those formulas used to date which are low in fat have proteins as free amino acids, which are of poor physiologic value. These formulas are generally hypertonic to blood, normally over 450 mOs/kg $H_2O$. As the stomach empties hypertonic solutions slower than solutions which have an osmolality closer to blood levels, the fat content and high osmolality of the existing enteral formulas contribute to poor tolerance, delayed gastric emptying, pulmonary aspiration, poor wound healing and preclude the patient from meeting the caloric goals. Patients who do not tolerate tube feeding diets must be given total parenteral nutrition, which is more costly, has a higher associated risk of serious complications such as serious infections, and requires expensive laboratory tests to monitor the clinical condition of the patient while receiving the therapy.

Although there are over 100 commercially-available tube feeding formulas, there are none which are low in fat and contain partially hydrolyzed protein. Most formulas contain 30% to 40% of the total calories from fat, with the remainder of the non-protein calories being carbohydrate. The fat often consists of variety of long chain triglycerides, which are difficult to digest and may contribute to diarrhea and abdominal pain. Many formulas also contain medium chain triglycerides. Medium chain triglycerides are easier to absorb, but they still empty slower than protein and carbohydrate from the stomach. There are a couple of products which are extremely low in total fats, but contain all of the protein in the form of free amino acids, rather than in the intact or partially hydrolyzed state. The free amino acids cause the osmolality of the formula to increase over formulas where protein is in the intact state. As noted, high osmolality solutions empty at a slower rate than solutions with osmolalities closer to blood, leading to potential aspiration problems. Today, there are no products on the market which are both low in fat (less than 10 grams per liter) and low in osmolality (less than 500 mOs/kg $H_2O$).

Thus, a need exists for an improved enteral formula which provides sufficient calories and nutrients but is low in fat and not hypertonic to blood.

Accordingly, an object of the invention is to provide an improved enteral formulation which provides high quality nutrition to critically ill patients while increasing tolerance and reducing the risk of pulmonary aspiration.

Another object of the invention is to provide a method of minimizing the risk or pulmonary aspiration and/or gastrointestinal dysfunction in critically ill patients by administering the enteral formulation of the invention which is low in fat and not hypertonic to blood.

Another object of the invention is to control blood sugar levels of critically ill patients by administering the enteral formulation of the invention which is low in fat, not hypertonic to blood and contains corn starch in the range of 1–10 grams/per liter of formulation.

A still further object of the invention is to provide a method for treating hypercatabolic patients by administering the enteral formulation of the invention which is low in fat and not hypertonic to blood.

These and other objects and features of the invention will be apparent from the following description and from the claims.

SUMMARY OF THE INVENTION

The present invention features an improved enteral formulation for the treatment of critically ill patients which is low in fat content, with the osmolality of the formula controlled to be between about 250 and 500 mOs/kg $H_2O$, more preferably between about 300 and 400 mOs/kg $H_2O$, and most preferably is about 300 mOs/kg $H_2O$.

The improved enteral formulation includes between about 2 and 4 grams of fat per 1,000 ml of the enteral formulation, more preferably no more than about 3 grams of fat (with a caloric contribution of about 27 kcal). The preferred fat is safflower oil, or other oils high in linoleic acid content. The preferred fat or oils to be used are those rich in polyunsaturated fatty acids such as corn oil, fish oil, or soy oil.

The improved enteral formulation further includes between about 50 and 100 grams of a protein hydrolysate per 1,000 ml of the enteral formulation, preferably about 70 grams of the protein hydrolysate (with a caloric contribution of about 280 kcal). The protein hydrolysate are preferably partially hydrolyzed in nature and include a substantial fraction of variable chain length peptides, e.g., medium or short chain peptides, e.g., di- and tri-peptides, but has less than about 10% free amino acids, more preferably less than about 5% free amino acids. In a preferred embodiment, only the highest biological value proteins are hydrolyzed, e.g., whey, lactalbumin, casein, egg white, egg solids, soy, or delactosed milk solids. In other preferred embodiments, the protein source is lactose-free, and free amino acids are preferably avoided in the enteral formulation of the invention.

In another aspect, the invention features enteral formulations including, in addition to low fat and the protein hydrolysate, carbohydrates, preferably between about 160 and 250 grams of carbohydrates per 1,000 ml of the enteral formulation, more preferably about 180 grams of carbohydrates (with a caloric contribution of about 720 kcal). The source of carbohydrates can be any simple or complex carbohydrate, e.g., monosaccharides, disaccharides, or oligosaccharides. The final osmolality of the enteral formulation is preferably controlled to be between about 250 to 500 mOs/kg $H_2O$, more preferably between about 300 and 400 mOs/kg $H_2O$, most preferably about 300 mOs/kg $H_2O$. Additional carbohydrate as corn starch is a preferred carbohydrate source to control blood glucose, with about 1 to 10 grams of corn starch added per 1,000 ml of enteral formulation, or in a preferred range, about 3 to 6 grams of corn starch is added per 1,000 ml of enteral formulation. The addition of 3 to 6 g. of corn starch per liter of the enteral formulation of the invention should be useful in controlling blood glucose levels of critically ill patients who frequently have elevated blood sugar levels.

In yet another aspect, the invention features enteral formulations including, in addition to the components described above (e.g., a low fat content, a protein hydrolysate and carbohydrates), sodium and potassium which may be included from any suitable salt, preferably in the amount ranging from about 10 to 40 mEq/L each, most preferably in the amount of about 20 mEq/L each, and most preferably mainly in the form of the chlorine salts.

The invention also features enteral formulations which include, in addition to the components described above, vitamins and minerals in accordance with, or approximately, the Recommended Dietary Allowance (RDA), now called the Reference Daily Intake (RDI). The enteral formulation of the invention can also contain nutrients not recommended by the RDA, e.g., beta-carotene, carnitine, and taurine.

Any enteral formulation preferably includes essential amino acids, essential fatty acids, and/or essential vitamins and minerals, and/or non-essential vitamins and minerals. The enteral formulations of the present invention may be in the form of a dietary supplement or used as a total enteral feeding regimen. If the latter, these essential nutrients are required while even in a supplement, the addition insures that the patient is obtaining these nutrients.

The invention also features a method of minimizing the risk of pulmonary aspiration in critically ill patients by administering a diet containing an improved enteral formulation which is low in fat content and contains a protein hydrolysate, wherein the osmolality of the formula is controlled to be between about 250 and 500 mOs/kg $H_2O$, more preferably between about 300 and 400 mOs/kg $H_2O$, and most preferably is about 300 mOs/kg $H_2O$.

In another aspect, the invention also features a method of improving nutritional status of critically ill patients by administering to such patients a diet containing an improved enteral formulation which is low in fat content and contains a protein hydrolysate, wherein the osmolality of the formula is controlled to be between about 250 and 500 mOs/kg $H_2O$, more preferably between about 300 and 400 mOs/kg $H_2O$, and most preferably is about 300 mOs/kg $H_2O$.

The method of the invention is particularly useful for patients who are critically ill for a variety of reasons; for example, the critical illness may be due to surgery, burns, trauma, cancer, AIDS, multisymptom organ failure, sepsis or inflammatory process, or the individuals may have an infection at the time of the administration of the diet or may be at high risk of infection due to some immunocompromise. Individuals at risk of infection include those suffering with secondary immunosuppression due to chemotherapy or diabetes mellitus, protein-malnourished patients, or patients undergoing surgery, e.g., abdominal or thoracic surgery.

In yet another aspect, the invention also features a method of minimizing the risk of gastrointestinal dysfunction in critically ill patients by administering a diet containing an improved enteral formulation which is low in fat content and contains a protein hydrolysate, wherein the osmolality of the formula is controlled to be between about 250 and 500 mOs/kg $H_2O$, more preferably between about 300 and 400 mOs/kg $H_2O$, and most preferably is about 300 mOs/kg $H_2O$.

The following description and non-limiting examples further elucidate the invention.

DETAILED DESCRIPTION OF THE INVENTION

The enteral formulation of the invention is made by blending fat, a protein hydrolysate, carbohydrates, and any additional additives, and homogenizing the mixture into a stable emulsion.

The fat source of the enteral formulation of the invention may comprise a mixture of safflower oil, MCT oil (medium chain triglycerides) and soy oil, or combinations that at least provide adequate amounts of essential fatty acids, e.g., linoleic or alpha linoleic acids (such as safflower oil or sunflower oil), as well as omega-3 or omega-9 fats. Examples of other suitable fat sources include corn oil, coconut oil, sunflower oil, menhaden oil, peanut oil, fish oil, canola oil and olive oil. However, the use of safflower oil is preferred because it has the highest percentage of the essential fatty acid, linoleic acid. Three grams per liter of safflower oil has been shown to be nutritionally sufficient without any evidence of essential fatty acid deficiencies.

The protein hydrolysate may be any suitable partially hydrolyzed protein or protein hydrolysate utilized in a nutritional formula such as soy protein hydrolysate, casein hydrolysate, whey protein hydrolysate, animal and vegetable protein hydrolysates, partially hydrolyzed whey, casein or soy proteins, and mixtures thereof. Soy or casein protein hydrolysates comprising a substantial proportion of variable chain length peptides, e.g., medium chain and short chain peptides, e.g., di- and tri-peptides, but having less than about 10% free amino acids, preferably less than about 5% free amino acids, are preferred. This minimizes the osmolality of the solutions (greater than 500 mOs/kg $H_2O$) to avoid a slower emptying rate than solutions with higher osmolalities as compared to blood and may contribute to pulmonary aspiration of gastric content. For greatest use, the protein source should be lactose-free so it can be used for lactose intolerant patients.

When choosing a protein source, the biological value of the protein should be considered first, with the highest biological values being found in casein, whey, lactalbumin, egg albumin, and whole egg proteins. Next, the cost should be considered, the lowest cost with the best biological value being the best combination. There is evidence to suggest that short chain peptides (di- and tri- peptides) are preferentially absorbed. However, too much of these short peptides in a protein hydrolysate increases the osmolality of the enteral formulation. Mixtures of di- and tri- peptides and longer chain peptides are preferred, allowing for high biological proteins and maintaining a low cost. In some specific disease states, such as cardiac failure, renal disease, and liver impairment, patients will benefit from diets which are low or devoid of selected micronutrients such as sodium (cardiac), potassium, magnesium, and phosphorus (renal), and sodium (liver). In these cases, hydrolyzed protein will be selected on the basis of the micronutrient content as well as biological value and cost.

The source of carbohydrate may be any simple monosaccharides, disaccharides, oligosaccharides, or complex carbohydrates. Examples include fructose, maltodextrin, corn syrup and hydrolyzed corn starch. Carbohydrate sources which may be utilized in the enteral formulation of the invention include hydrolyzed or nonhydrolyzed starches. An examples of a starch that can be used in the enteral formulation is corn. Corn starch in a 5 grams per day dose has been shown to minimize nocturnal hypoglycemia in patients with diabetes. Thus, between 3 to 6 grams of corn starch is added per 1,000 ml of enteral formulation to control blood glucose levels in critically ill patients.

Patients with critical illness and hypercatabolism often experience secondary problems. These conditions will benefit from modifications to the low fat, hydrolyzed protein formulation of the invention. For example, patients with renal disease should avoid potassium, magnesium, and phosphorus in their diet. Thus, the enteral formulation of the invention could be made with lesser amounts of these micronutrients or can be devoid of them altogether. Patients with liver and cardiac disease should avoid sodium and a low sodium version of the enteral formulation of the invention could also be prepared. Patients with the aforementioned conditions and multisystem organ failure would benefit from less fluid in the diet so that a more concentrated diet could be created. In these embodiments, the formulation could have 1.2 to 1.5 kcal/ml rather than a typical 1.0 kcal/ml.

Emulsifiers may be added for stability purposes to the enteral formulation of the invention, e.g., emulsifiers such as soybean phospholipids.

The enteral formulation may also contain a stabilizer such as λ-carrageenan. λ-carrageenan increases the viscosity of the formula without forming a gel structure, thus retarding the precipitation of insoluble calcium and phosphorus salts if included in the formula. Xanthan gum or other standard stabilizers may also be used as a stabilizer in the same fashion as λ-carrageenan.

While the enteral formulation of the invention is preferably provided in a ready-to-feed form, it may also be concentrated by increasing the percent total solids of the formula or made in powder form, both procedures being well known to those skilled in the art. The concentrate or powder are then reconstituted for feeding by adding water (tap or deionized-sterilized water).

Certain terms used herein are described below for clarity.

As used herein, the term "protein hydrolysate" refers to a peptide preparation which contains less than about 10% free amino acids, more preferably less than about 5% free amino acids, and consists substantially of peptides that are less than 40 amino acids in length with more than 50% of the peptides having molecular weight of less than 5,000 KD, more preferably with about 90–95% of the peptides having molecular weight of less than 5,000 KD. The peptide breakdown of a preferred protein hydrolysate preparation useful in the invention is shown in Table 2.

As used herein, the term "critically ill patients" refers to patients who are suffering from a total or partial dysfunction of the gastro-intestinal tract due to disease or stress of injury such as surgery, cancer, acute diabetes, AIDS, malnutrition, trauma or sepsis. The term "critically ill patients", as used herein, is also intended to include hypercatabolic patients. These critically ill individuals are often hospitalized and must receive most or all of their daily nutritional requirements parenterally and/or enterally in order to sustain protein synthesis and to minimize the likelihood of becoming malnourished, to maintain nutritional status, or to improve nutritional status.

As used herein, the term "gastrointestinal dysfunction" refers to gastrointestinal symptoms such as those experienced by patients who are receiving enteral nutrition. Symptoms can include abdominal pain, cramping, bloating, diarrhea and/or steatorrhea. Usually these symptoms are provoked by high fat content of tube feeding formulas, which causes formula to empty very slowly form the patient's stomach. Certain fats are poorly absorbed and may contribute to diarrhea and steatorrhea.

As used herein, the term "pulmonary aspiration" refers to a condition in which gastric content of the stomach is aspirated into the lungs of a patient receiving enteral nutrition. This condition is caused by high fat or hypertonic formulas which empty very slowly from the patient's stomach.

EXAMPLE 1

This Example describes an enteral formulation of the invention. The basic ingredients of the enteral formulation are set forth in Table 1.

TABLE 1

| Ingredient | Amount per 1,000 ml (grams) | Caloric contribution (kcal) | % of total caloric contribution |
| --- | --- | --- | --- |
| fat (safflower oil) | 3 | 27 | 2.63 |
| protein (hydrolyzed) | 70 | 280 | 7.79 |
| carbohydrate | 180 (3–6 g of which are corn starch) | 720 | 70.1 |

Total kcal per 1,000 ml of formula=1,027

1. Osmolality of the formula=350–500 mOs/kg $H_2O$
2. Protein source=Protein hydrolysates are available from New Zealand Milk Products, Santa Rosa, Calif. (e.g., casein hydrolysate (ref. no. MPH 955) or whey protein hydrolysate (ref. no. WPH 930)).
3. Carbohydrate source=carbohydrates can be obtained from sugars, hydrolyzed corn starch, oligosaccharides, fructose, corn syrup or sucrose.

TABLE 2

Typical protein/peptide analysis of the protein hydrolysate to be used in the enteral formulation of the invention Absorbance from molecular weight profile in kilodaltons (KD) using HPLC analysis of peptides using TSK-Gel G2000 $SW_{xl}$ column (approximate mol. weight of a single amino acid is 133).

| | |
| --- | --- |
| 10,000–20,000 | 0.8% |
| 5,000–10,000 | 2% |
| 2,000–5,000 | 15% |
| 1,000–2,000 | 23% |
| 500–1,000 | 27% |
| <500 | 32% | di-and tri-peptides are in the range less than <400 KD.

The possible additives to the enteral formulation of the invention are set forth in Table 3.

TABLE 3

ADDITIVES

| Ingredient | Amount per 1000 ml of formula |
|---|---|
| Vitamin A (as palmitate) | 5,000 I.U. |
| Vitamin D | 400 I.U. |
| Vitamin E (as acetate) | 30 I.U. |
| Vitamin K | 60 mg |
| Vitamin C (as corbic acid) | 100 mg |
| Folic Acid | 400 mcg |
| Thiamin (as hydrochloride) | 2.0 mg |
| Riboflowin | 2.3 mg |
| Vitamin $B_6$ (as pyridoxine hydrochloride) | 2.7 mg |
| Vitamin $B_{12}$ (as cyanocobalamin) | 8 mcg |
| Niacin (as niacinamide) | 27 mg |
| Choline | 400 mg |
| Biotin | 400 mcg |
| Pantothenic Acid (as calcium pantothenate) | 13 mg |
| Sodium | 40 mg |
| Potassium (as chloride) | 40 mg |
| Chloride | 80 mg |
| Phosphorus | 670 mg |
| Magnesium (as gluconate) | 270 mg |
| Copper (as gluconate) | 1.3 mg |
| Zinc (as sulfate) | 15 mg |
| Iron (as ferrous sulfate) | 12 mg |
| Selenium (as sodium selenite) | 47 mcg |
| Chromium (as chromic acetate) | 67 mcg |
| Molybdenum (as sodium molybdate) | 100 mcg |

Other additives may include taurine, histidine, manganese (as sulfate), iodine (as potassium iodide) and carnitine (as L-carnitine).

EXAMPLE 2

This example outlines one possible processing procedure for formulating the enteral formulation of the invention.

This procedure can be carried out manually by a pharmacist or other trained personnel (kitchen help). The method of making the enteral formulation of the invention can best be carried out by shaking or using a mixing machine, e.g., a Waring mixer or a general household blender.

The method can be carried out using a series of sequential steps and the mixer formulates the final enteral solution. The major steps involved in the preparation are: (1) preparation of the carbohydrate premix; (2) preparation of the fat base; (3) preparation of the protein hydrolysate premix; (4) preparation of the vitamin/mineral premix; and (5) blending the two aqueous premixes (3 and 4) with the fat base.

The following procedure can be used to prepare a lab sized test solution of about 1–5 liters of the enteral formulation of the invention. To a kettle containing 2,000 ml of deionized water, add the carbohydrate (900 g.) and the emulsifier and blend and heat to 165° C. To this blend add safflower oil (15 g.) and homogenize at 500 PSI, then at 3000 PSI. This combination forms an emulsion which is the fat base. Prepare the aqueous protein hydrolysate (350 g.) premix in 650 ml of deionized water and the vitamin mineral premix (containing combination of additives from Table 3) in 800 ml of deionized water. Add the two aqueous premixes to the mixer and blend together. Finally add the concentrated fat base and deionized water to final volume of 5 liters to the mixer and mix for 10 minutes or until the mixture is emulsified.

The enteral formulation of the invention may be administered via a nasogastric, nasointestinal, esophagostomy, gastrostomy, or jejunostomy feeding tube. Because of its homogeneity and low viscosity small bore feeding tubes (#8 French tube) may be used to optimize patient tolerance. The diet should be given at room temperature by continuous drip technique, or using suitable infusion pump. At about 1 kcal per ml dilution, the composition supplies most of the daily fluid requirements. Additional fluids can be given when necessary to maintain hydration and adequate urine output. The enteral formulation can also be administered orally as a flavored drink served chilled over ice.

The foregoing examples is purely illustrative and is not intended to be the limitation of the invention. Those skilled in the art can determine other modifications on the enteral formulations used herein. Such modifications are included within the following claims.

What is claimed is:

1. An enteral formulation for critically ill patients comprising:

about 2–4 g/l fat;

about 50–100 g/l protein hydrolysate derived from protein selected from the group consisting of casein, whey, lactalbumin, egg white, egg white solids and delactosed milk solids;

about 160–250 g/l carbohydrate of which from about 3 to about 10 g/l of carbohydrate is corn starch; and water, whereby the osmolality of said enteral formulation is controlled to be 250–500 mOs/kg $H_2O$.

2. The enteral formulation of claim 1, wherein the osmolality is controlled to be between about 300–400 mOs/kg $H_2O$.

3. The enteral formulation of claim 1, wherein the osmolality is controlled to be about 300 mOs/kg $H_2O$.

4. The enteral formulation of claim 1, wherein the fat content is about 3 g/l fat.

5. The enteral formulation of claim 1, wherein the fat is selected from the group consisting of safflower, sunflower, corn, olive, menhaden, coconut oil, canola oil, peanut oil and mixtures thereof.

6. The enteral formulation of claim 5, wherein the fat is selected from high linoleic and alpha linoleic acid safflower and sunflower oil.

7. The enteral formulation of claim 5, wherein the fat provides all essential fatty acids.

8. The enteral formulation of claim 1, wherein 3–6 g/l of the total carbohydrates are derived from corn starch.

9. The enteral formulation of claim 1, wherein the source of carbohydrates supplies monosaccharides, disaccharides, and oligosaccharides.

10. The enteral formulation of claim 1, wherein the formulation further comprises about 10–40 mEq/l of a salt containing Na+ions and about 10–40 mEq/l of a salt containing K+ions.

11. The enteral formulation of claim 1, wherein the formulation further comprises a vitamin or mineral.

12. The enteral formulation of claim 1, wherein said protein hydrolysate comprises less than about 10% of free amino acids.

* * * * *